United States Patent [19]

Campbell et al.

[11] 4,232,042
[45] Nov. 4, 1980

[54] DI-CARBOXYLIC ACID DERIVATIVES

[75] Inventors: Alexander C. Campbell, Falkirk; Colin L. Hewett, Glasgow, both of Great Britain; Filippus J. Zeelen, Heesch, Netherlands

[73] Assignee: Akzona Incorporated, Asheville, N.C.

[21] Appl. No.: 729,509

[22] Filed: Oct. 4, 1976

[30] Foreign Application Priority Data

Oct. 7, 1975 [GB] United Kingdom ............... 41042/75

[51] Int. Cl.$^3$ .................. C07C 57/38; C07C 69/616; A61K 31/19
[52] U.S. Cl. ............... 424/308; 260/465 D; 560/55; 560/75; 560/81; 562/465; 562/478; 562/488; 564/156
[58] Field of Search ............ 260/515 P, 469, 475 SC; 560/8, 81; 562/448; 424/307, 318

[56] References Cited

U.S. PATENT DOCUMENTS 2,497,673 2/1950 Kirk ................................. 260/515 P
3,385,863 5/1968 Wick et al. ...................... 260/515 P

OTHER PUBLICATIONS

Jaunin et al., as cited in Chem. Abstracts, 52, p. 10025, (1958).
Abell et al., J.A.C.S., 76, pp. 4406–4412, (1954).
Allinger et al., J.A.C.S., 76, pp. 2362–2367, (1954).
Cram et al., J.A.C.S., 73, pp. 5691–5695; 5698–5703, (1951).

Primary Examiner—Jane S. Myers
Attorney, Agent, or Firm—Robert H. Falk; Francis W. Young; Charles A. Wendel

[57] ABSTRACT

The invention relates to novel compounds of general formula I:

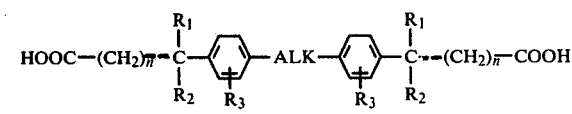

and salts, esters and amides thereof, in which
 $R_1$ and $R_2$ represent hydrogen, alkyl or alkenyl (1–4 C),
 $R_3$ represents hydrogen, halogen, hydroxy, alkyl (1–4 C) or alkoxy (1–4 C),
 n has the value 0, 1 or 2 and
 ALK is a saturated or unsaturated hydrocarbon radical with 3–12 carbon atoms, in which a straight carbon chain in between the benzene rings is present, containing 3–8 carbon atoms, and
the dotted line indicates an optional extra bond between the first and second carbon counted from the phenyl ring, in case of an extra bond the group $R_2$ and one hydrogen attached to said second carbon being absent, having valuable hypocholesterolaemic and hypotriglyceriolaemic properties.

4 Claims, No Drawings

DI-CARBOXYLIC ACID DERIVATIVES

The invention relates to novel biologically active $\omega,\omega^1$ saturated or unsaturated alkylene-di-phenylalk(en)yl-carboxylic acids and derivatives thereof, to processes for the preparation of these compounds and to a pharmaceutical preparation containing these compounds as the active component. In particular, the invention relates to novel compounds of general formula I:

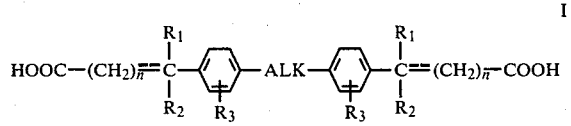

and salts, esters and amides thereof, in which $R_1$ and $R_2$ represent hydrogen, alkyl or alkenyl (1–4 C), $R_3$ represents hydrogen, halogen, hydroxy, alkyl (1–4 C) or alkoxy (1–4 C), n has the value 0, 1 or 2 and ALK is a saturated or unsaturated hydrocarbon radical with 3–12 carbon atoms, in which a straight carbon chain in between the benzene rings is present, containing 3–8 carbon atoms, and the dotted line indicates an optional extra bond, between the first and second carbon counted from the phenyl ring, in case of an extra bond the group $R_2$ and one hydrogen attached to said second carbon being absent.

The compounds according to the invention have valuable hypocholesterolaemic and hypotriglycerolaemic properties.

The compounds of the invention may be prepared according to well-known methods in actual use or described in the literature.

A very convenient synthesis starts from a compound of the general formula II:

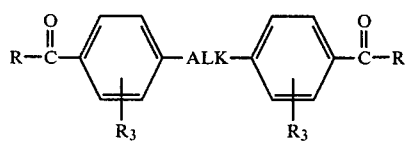

in which $R_3$ and ALK have the meanings defined before and R stands for a methyl, ethyl or propyl group. Compounds of the general formula I, in which n=0 and $R_1$ and $R_2$ are hydrogen can be prepared from a compound of formula II by carrying out the well-known Willgerodt reaction, followed by hydrolysis of the compound thus obtained. The phenylalkylketones of formula II undergo a combined oxidation and rearrangement to $\omega$-phenylalkylthioamides when heated with ammoniumpolysulphide ($NH_4S_x$) or with sulphur and a secondary amine, such as morpholine. The thioamides thus obtained are hydrolysed in the usual manner with water in the presence of an acid or base. An isolation of the intermediate thio-amides is possible but not strictly necessary.

Compounds I obtained in this manner, in which n is 0, may further be converted into other compounds of formula I by alkylating the $\alpha$-carbon atom of the carboxy-methyl moiety and/or by chain-elongation of the carboxy-methyl moiety, as will be shown below.

Another suitable method for the preparation of the compounds of formula I, which is more generally applicable, starts from a compound of the general formula III:

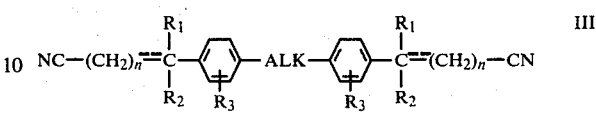

in which $R_1$, $R_2$, $R_3$, n, ALK and the dotted line have the meanings indicated above.

The compounds of the invention are prepared by hydrolysing III in a manner commonly used for hydrolysis of a nitrile group. The nitriles of formula III react with water in the presence of a relatively strong acid or base to give first the amide of formula I, which can then be either isolated or hydrolysed further to the corresponding carboxylic acid. The nitriles can also directly be converted to esters by reaction of an alcohol preferably under acidic conditions.

A further method for the preparation of compounds I in which n is 0 and $R_1$ and/or $R_2$ is (are) other than hydrogen starts from the corresponding compound I in which at least one of the groups $R_1$ or $R_2$ is hydrogen, namely a compound of the general formula IV:

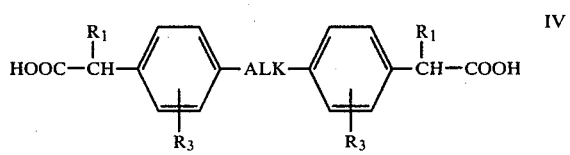

or an ester or amide thereof, in which $R_1$, $R_3$ and ALK have the meanings above indicated.

A compound IV or an ester or amide thereof, whereby the ester is to be preferred, is reacted with an alkali-metal, such as lithium, sodium or potassium, in a suitable solvent, with an alkalimetal-amide or hydride, such as sodiumhydride, lithiumamide, sodamide or lithiumdialkyl-amide, or with an organo-alkalimetal compound, such as alkyllithium, alkylsodium, phenyllithium, tritylithium, phenylsodium or phenylpotassium. Preferred reagents in this respect are: butyllithium, sodamide and preferably lithium-di-isopropylamide.

In this reaction an alkalimetal replaces an $\alpha$-hydrogen atom of the carboxymethyl moiety. The alkalimetal derivative thus obtained is subsequently reacted with hydrocarbon-halide (1–4 C), such as methyliodide, methylbromide, methylchloride, ethyliodide, propyliodide, butylbromide or allylbromide.

Another method for the preparation of compounds I in which n is 0 and $R_1$ and/or $R_2$ is (are) other than hydrogen consists of halogenating a compound of formula IV or an ester, amide or acidhalide thereof. In this reaction the $\alpha$-hydrogen atom of the carboxymethyl moiety is replaced by halogen. The halogenation is preferably carried out with N-bromosuccinimide (NBS) or with bromine. If the free acid of formula IV is used as starting product in the halogenation with bromine the reaction is preferably carried out in the presence of $SOCl_2$.

Starting from an acidhalide derivative of IV the halogenation affords an $\alpha$-halo-acid halide that can easily be converted to the α-halo-acid or -ester by the action of water or alcohol.

The α-halo compound thus obtained is subsequently treated with a hydrocarbon-alkalimetal, such as methyllithium, butyllithium, methylsodium, ethylsodium, ethyllithium, etc.

Compounds of the general formula I, in which n is 1 or 2 can further be prepared from the corresponding compound I, in which n=0, by any well-known method for chain-elongation.

For example the carboxyl group of a compound of formula I, in which n=0, can be reduced with diborane to the corresponding alcohol and subsequently halogenated to obtain the corresponding halo-compound. Thus halo-compound can be either converted with sodiumcyanide to the corresponding nitrile followed by hydrolysis or reacted with lithium or magnesium yielding the corresponding lithium compound or magnesium halide compound respectively. The latter lithium or "Grignard" compound obtained is reacted with $CO_2$ in the usual manner and then hydrolysed. In both cases a compound of formula I is obtained, in which n is 1.

Starting from a compound I in which n=1 the corresponding compound I with n=2 is obtained in the same manner as described above.

A more direct method for preparing compounds I, in which n is 1 or 2 consists of a reaction of a compound of the general formula II A:

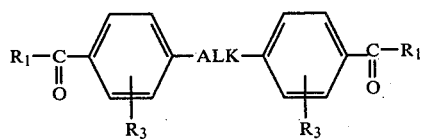

in which $R_1$, $R_3$ and ALK have the aforesaid meanings, with a reagent of the general formula V:

$$Ph_3P=CH—(CH_2)_m—Y \qquad V$$

in which m has the value 0 or 1, Ph stands for an aryl, cycloalkyl or alkyl group and preferably a phenyl group, and Y represents a carboxyl, esterified carboxyl or carbo-amide moiety. This reaction is carried out under conditions which are commonly applied in Wittig reactions.

The above Wittig-reaction results in a compound according to the general formula VI:

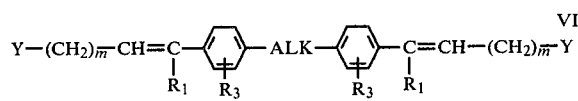

in which $R_1$, $R_3$, m, ALK and Y have the meanings indicated before.

These compounds VI are part of the compounds according to the invention.

Obviously, the said Wittig reaction may also be carried out with a Wittig reagent of formula V, in which Y represents a cyano (CN) moiety. The resulting compound of formula VI, in which Y is CN, is in that case covered by the aforesaid compound of general formula III, and has to be hydrolysed to obtain the acid of formula I.

The compounds of formula VI, in which Y is a carboxyl, esterified carboxyl or carbo-amide moiety as well as all (other) compounds of formula I, in which ALK is an unsaturated hydrocarbon, can further be reduced to a saturated compound according to the general formula I, preferably by catalytic hydrogenation in the usual manner (e.g. hydrogen in the presence of a catalyst such as Pt, Pd, $PtO_2$, Pd/C or Raney nickel) or with a complex-metalhydride, such as $LiAlH_4$ or diboran.

The preparation of the compounds according to the invention as well as the preparation of the starting products mentioned before are briefly summarized in the flow sheet on the next page.

Flow sheet

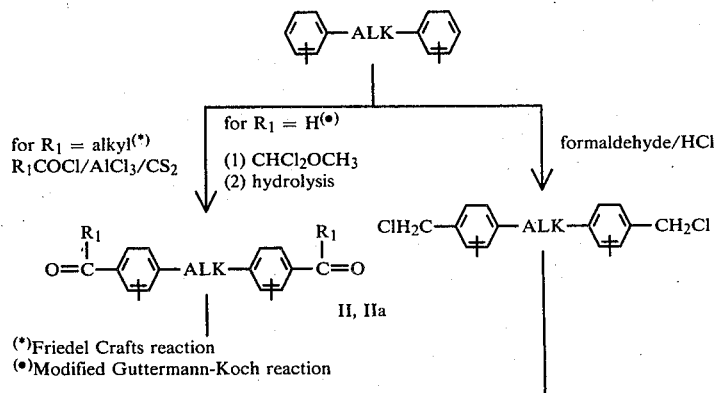

(*)Friedel Crafts reaction
(•)Modified Guttermann-Koch reaction

-continued
Flow sheet

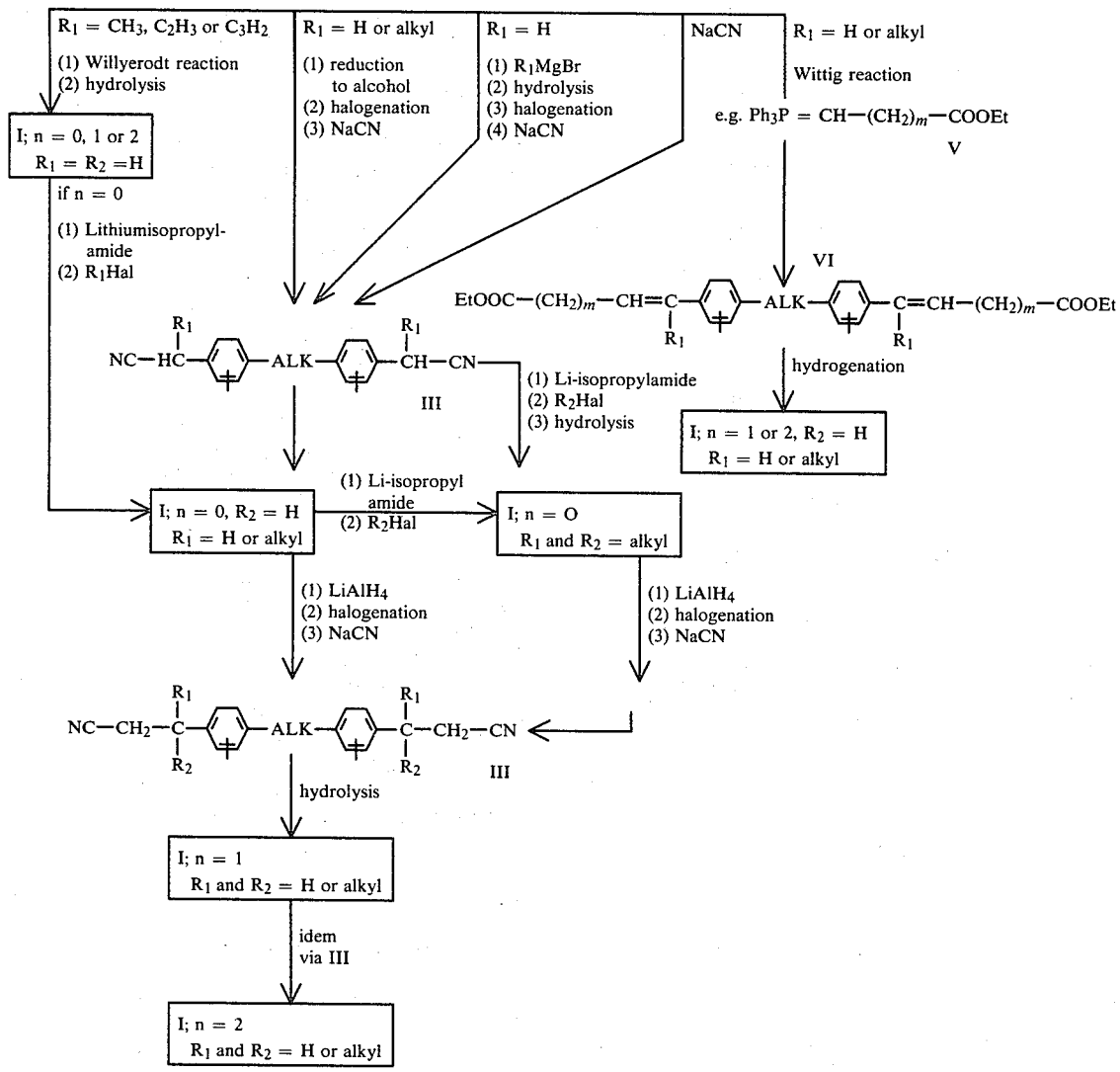

The compounds of the invention, in which $R_1$ is alkyl and $R_2$ is hydrogen, contain an asymetric centre in both carboxy-alkyl chains of the molecule, so that besides an optically inactive mixture, also optically active enantiomers of formula I and an optically inactive "meso-isomer" of formula I can be prepared. The mixture as well as the said stereo-isomers I are numbered along the compounds of the invention.

The mixture consisting of two optically active enantiomers (d- and l-form) and the optically inactive mesoform may be separated in the usual manner. The meso-isomer I can be isolated from the mixture by physical separation techniques, such as fractional crystallisation, column chromatography, preparative thin layer chromatography, counter current distribution, etc. Both optically active isomers can be separated in a known fashion using an optically active base.

The same applies for optically-active and -inactive isomers originating from one or more asymetric centres in the saturated or unsaturated alkylene (ALK) moiety of formula I.

The derivatives of the compounds of formula I, namely esters, amides and salts, can be either obtained directly from the aforesaid reactions or prepared afterwards from the corresponding carboxylic acid of formula I.

The pharmaceutically acceptable salts of the present invention are obtained by reacting the free acid I with a suitable base, such as alkalimetal- or alkaline-earthmetal bases, e.g. NaOH, KOH, $Mg(OH)_2$, other metalbases such as aluminiumhydroxide or organic bases, in particular nitrogen-containing organic bases such as pyridine, piperidine, pyridoxine, etc.

The esters of the present invention are aliphatic (including cyclo-aliphatic), araliphatic, aromatic or heterocyclic esters, in particular the lower aliphatic and phenyl-aliphatic esters, in which the aliphatic group contains 1-6 carbon atoms, such as the methyl-, ethyl-, propyl-, butyl-, isopropyl-, sec.butyl-, phenylethyl-, phenylpropyl-, cinnamyl- or benzyl ester.

The esters are prepared in the usual manner by reacting the free acid of formula I or a functional derivative thereof, such as an acidhalide or anhydride, with the alcohol in question. The amides of the invention are preferably unsubstituted or lower alkyl (1-4 C) substituted amides. They are prepared from the free acid I or functional derivative thereof, such as an acidhalide, anhydride or ester, in the usual manner for the preparation of an amide.

The novel compounds according to the invention have, as already noted, valuable hypocholesterolaemic and hypotriglyceriolaemic properties, and can thus be applied in the treatment of atherosclerosis.

Preferred compounds among the compounds according to general formula I have the formula:

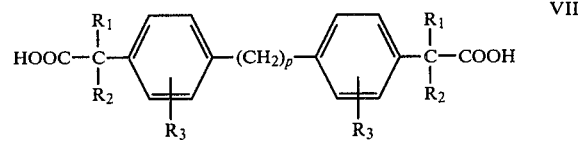

VII and salts, esters or amides thereof, in which $R_1$, $R_2$ and $R_3$ have the meanings above indicated and p has the value 3 or 4.

The compounds of formula VII possess excellent hypocholesterolaemic and hypotriglyceriolaemic properties.

Other compounds according to the invention (formula I) show a dissociation between both properties in favour of the triglyceride-lowering effect.

Among the compounds according to formula VII those compounds, in which both $R_1$ and $R_2$ represent the same alkyl group, preferably a methyl group, and those compounds, in which $R_1$ is alkyl and $R_2$ is hydrogen are to be preferred.

The compounds of the invention may be administered enterally or parenterally, preferably in a daily dosage of from 0.01–25 mg per kg body weight.

Mixed with suitable excipients the compounds I may be compressed into solid dosage units, such as pills, tablets, coated tablets or be processed into capsules. By means of suitable liquids and optionally other excipients the compounds I can also be applied as an injection preparation in the form of solutions, suspensions or emulsions.

The following examples serve to illustrate the preparation of the compounds according to the present invention.

EXAMPLE 1

1,3-Bis-(4-carboxymethyl-phenyl) propane a. 1,3-bis-(4-acetylphenyl) propane.

To a stirred suspension of powdered $AlCl_3$ (238 g) in 260 ml $CS_2$ is added a solution of 85,7 g 1,3-di-phenyl-propane in 260 ml $CS_2$. 127 ml Acetylchloride (140 g) is added to the mixture within about one hour. After being stirred for 1.5 hr. at ambient temperature the solvent ($CS_2$) is distilled off. The residue is then hydrolysed by a careful addition of small pieces of ice. The mixture is subsequently stirred for one hour and then filtered to remove the crystalline product from the reaction mixture. The crystals obtained are dissolved in methylenechloride, after which the solution is washed with a 5% sodiumbicarbonate solution and water successively and then dried. Evaporation of the solvent yields 120.5 gr. of the crystalline product, which is recrystallised from acetone:hexane (1:4). Final yield 86 g; melting point 84°–86° C.

b. 1,3-bis-(4-carboxymethyl-phenyl) propane.

80 g of the compound obtained in a. is dissolved in 217 ml morpholine. While stirring 31 g sulphur are added to the solution after which the reaction mixture is refluxed overnight. The coloured solution is then poured into 1.2 liter ethanol of 60°–70° C. The temperature of the mixture is slowly cooled down, while stirring. During this process a precipitate is formed that is filtered off and is washed with ethanol.

The precipitate is suspended in a mixture of 1250 ml ethanol and 500 ml water after which 275 ml is 10 N KOH is added. The mixture is refluxed overnight under nitrogen atmosphere, poured on to ice and then acidified with 6 N hydrochloric acid. The precipitate formed is filtered off, washed with water and dried. Yield 71 g. Melting point 213°–215° C.

EXAMPLE 2

1,3-bis-(4-carboxymethyl-phenyl) propane dimethylester 71 g of the acid obtained in Example 1 is esterified with 550 ml methanol and 45 ml $H_2SO_4$ at reflux temperature. After the addition of 150 g sodiumacetate methanol is removed from the reaction-mixture by evaporation. To the residue obtained 500 ml water is added, after which the mixture is extracted with ether. The ether-extracts are washed with a 5% $NaHCO_3$-solution and with water, after which the extracts are dried and evaporated. The residue (77 g) is recrystallised from methanol yielding 28 g of the title product; melting point 52°–53° C.

The mother-liquor is chromatographed over silicagel using the solvent system toluene:ethylacetate (9:1). In this manner an additional quantity (39 g) of the above methylester can be isolated; melting point 50°–52° C.

Esterification with phenylethylchloride yields the corresponding di-phenylethyl ester as an oil.

EXAMPLE 3

In the same manner as described in Example 1, the following compounds are prepared:

1. 1,4-bis-(4-carboxymethyl-phenyl)butane; m.p. 214°–217° C.
2. 1,5-bis-(4-carboxymethyl-phenyl)pentane; m.p. 197°–199° C.
3. 1,6-bis-(4-carboxymethyl-phenyl)hexane; m.p. 200°–203° C.
4. 1,7-bis-(4-carboxymethyl-phenyl)heptane; m.p. 182°–184° C.
5. 1,8-bis-(4-carboxymethyl-phenyl)octane; m.p. 184°–186° C.
6. 1,4-bis-(4-carboxymethyl-phenyl)-2,2,3,3-tetramethyl butane; m.p. 205°–208° C.
7. 1,3-bis-(4-carboxymethyl-phenyl)-2,2-dimethyl propane; m.p. 182°–185° C.
8. 1,3-bis-[4-(2-carboxy ethyl)phenyl]propane; m.p. 184°–186° C.

All compounds are additionally converted into their sodium salts; melting points over 270° C.

Compound 8 is prepared by using propionylchloride instead of acetylchloride as described in the Friedel-Crafts reaction of Example 1 a.

EXAMPLE 4

1,3-bis-[4-(1-carboxyl ethyl)phenyl]propane and esters and amide thereof.

108,5 ml 2 N methyllithium is added dropwise within about 10 minutes to a stirred solution of 21,9 g (28.4 ml) dry di-isopropylamine in 540 ml dry tetrahydrofuran at −10° C. under nitrogen atmosphere. After being stirred for 15 minutes at −10° C. the mixture is further cooled down to −78° C. At this temperature a solution of 24,6 g 1,3-bis-(4-carboxymethyl-phenyl) propane dimethyl ester (Ex. 2) in 90 ml tetrahydrofuran is added to the mixture, after which it is stirred for 1½ hr. Subsequently 56,8 g (24,9 ml) methyliodide is added to the mixture at −78° C., after which it is stirred for 1 hr. at −78° C. and about 15 minutes at −30° C. The solvent used is then evaporated, after which water (750 ml) is added to the residue. The aqueous mixture is acidified with 2 N HCl and then extracted with ether. The ether extracts are washed till neutral with a 5% sodium bicarbonate solution and with water. Evaporation of the solvent (ether) yields 27,3 g of the oily 1,3-bis-[4-(1-carboxy-ethyl)phenyl]propane dimethyl ester. Purification of this crude ester by column-chromatography over silica-gel using the solvent-system toluene-ethylacetate (98:2) yields 21,2 g of the pure oily ester.

A solution of 18 g of this ester in 180 ml methanol is refluxed with 25 ml 10 N KOH for 1½ hr. under nitrogen atmosphere.

The solvent is then evaporated and the residue is poured on to ice. The mixture is acidified with 6 N HCl, after which the precipitate formed is filtered off, washed and dried. Yield: 15.5 g. Melting point 140°–143° C.

Esterification with ethanol yields the di-ethyl ester of the title compound as an oily substance: $R_f$ in hexane-:acetone (9:1)=0.48 on $SiO_2$. By aminolysis of this ester the di-amide is obtained as a crystalline compound, melting point 181°–184° C.

EXAMPLE 5

In the same manner as described in Example 4 the following compounds are prepared:
1. 1,4-bis-[4-(1-carboxy-ethyl)phenyl]butane; m.p. 141°–143° C.;
2. 1,5-bis-[4-(1-carboxy-ethyl)phenyl]pentane; m.p. 109°–111° C.;
3. 1,6-bis-[4-(1-carboxy-ethyl)phenyl]hexane; m.p. 115°–120° C.;
4. 1,7-bis-[4-(1-carboxy-ethyl)phenyl]heptane; m.p. 100°–102° C.;
5. 1,8-bis-[4-(1-carboxy-ethyl)phenyl]octane; m.p. 116°–119° C.;
6. 1,3-bis-[4-(1-carboxy-ethyl)phenyl]-2,2-dimethyl propane; m.p. 185°–195° C.;
7. 1,3-bis[3-methyl-4-(1-carboxy-ethyl)phenyl]propane; m.p. 129°–130° C.;
8. 1,3-bis-[2-bromo-4-(1-carboxy-ethyl)phenyl]propane; m.p. 125°–127° C.

Additionally the sodium salts of the compounds 1–6 are prepared, melting points over 270° C.

EXAMPLE 6

In the same manner as described in Example 4, but using ethyliodide or allylbromide instead of methyliodide the following two compounds are prepared:
1,3-bis-[4-(1-carboxypropyl)phenyl]propane; m.p. 134°–136° C.;
1,3-bis-[4-(1-carboxybuten-3-yl)phenyl]propane (oil); $R_f$ in chloroform:methanol (9:1)=0.47 on $SiO_2$.

EXAMPLE 7

1,3-bis-[4-(2-carboxy isopropyl)phenyl]propane and esters thereof

In the same manner as described in Example 4 the compound 1,3-bis-[4-(1-carboxy-ethyl)phenyl]propane dimethyl ester (Ex. 4) is treated with lithium-di-iso-propylamide and methyliodide, after which the di-methyl ester thus obtained is hydrolysed to obtain the title compound. Melting point 171°–172° C.

Esterification of the acid obtained with ethanol yields the diethyl ester as an oily substance, $R_f$ in toluene:ethy-lacetate (95:5)=0.53 on $SiO_2$.

EXAMPLE 8

1,3-bis-[4-(1-carboxy isopropyl)phenyl]propane 4 g 1,3-bis-[4-(1-cyano isopropyl)phenyl]propane is added to 55 ml 50%-$H_2SO_4$ at a temperature of about 50° C.

The mixture is kept at about 100° C. for 6 hr. while stirring, and cooled down to ambient temperature. The mixture is then extracted with ethylacetate; the extracts washed with water to neutral and dried. Evaporation of the solvent yields a crude residue in about 85% yield, that is recrystallised from toluene/ethylacetate. Melting point 115°–117° C.

EXAMPLE 9

In the same manner as described in Example 8 are prepared by hydrolysis of the corresponding cyano-compound the following substances:
1,3-bis-(4-carboxy methyl-phenyl)propane, m.p. 213°–215° C.;
1,4-bis-(4-carboxy methyl-phenyl)butane, m.p. 214°–217° C.;
1,3-bis-[4-(2-carboxy ethyl)phenyl]propane, m.p. 184°–185° C.;
1,3-bis-[4-(1-carboxy ethyl) phenyl]propane, m.p. 140°–142° C.;
1,3-bis-[3-methyl-4-(1-carboxyethyl)phenyl]propane, m.p. 125°–129° C.;
1,3-bis-[4-(1-carboxy propyl)phenyl]propane, m.p. 135°–137° C.;
1,3-bis-[4-(2-carboxy isopropyl)phenyl]propane, m.p. 170°–172° C.;
1,3-bis-4-(2-carboxymethyl isopropyl)phenyl]propane (oil);
1,6-bis-(4-carboxymethyl-phenyl)hexane, m.p. 200°–202° C.;
1,8-bis-(4-carboxymethyl-phenyl)octane, m.p. 185°–186° C.;
1,3-bis-[4-(1-methyl-2-carboxy-ethenyl)phenyl]propane (oil);
1,4-bis-(4-carboxymethyl-phenyl)butadiene (oil);
1,4-bis-[4-(1-carboxyethyl)phenyl]butadiene (oil).

EXAMPLE 10

1,3-bis-[4-(1-methyl-2-carboxy-ethenyl)phenyl]propane diethyl ester.

A mixture of 11.35 g 1,3-bis-(4-acetylphenyl)propane and 52.8 g of the Wittig reagent ethoxycarbonylmethy-lene triphenylphosphorane is heated for one night at 170° C. under nitrogen atmosphere. The reaction mix-ture obtained is cooled down and chromatographed over a silicagel column with the aid of the solvent sys-tem hexane:acetone (9:1). Yield 9.5 g (55%) of the oily product. $R_f$ in hexane:acetone (75:25)=0.55 on $SiO_2$.

EXAMPLE 11

1,3-bis-[4-(1-carboxy-isopropyl)phenyl]propane diethyl ester.

To a solution of the compound obtained in Example 10 (6.5 g) in 700 ml methanol is added 2.5 ml 70% $HClO_4$ and 0.55 g 10% palladium on charcoal after which the mixture is hydrogenated (using a Parr apparatus). The mixture is then filtered and the filtrate is concentrated after having added 5 g of sodium-acetate. The concentrate is diluted with water and then extracted with ether. The ether extracts are washed with 5% sodiumbicarbonate solution and with water, after which the extract is dried and evaporated.

The residue is chromatographed over a $SiO_2$ column using the solvent system toluene:ethylacetate (98:2), yielding an oil product. Yield 3.5 g. $R_f$ in toluene:ethylacetate (9:1)=0.65 on $SiO_2$.

Hydrolysis of the said diethyl ester in the usual manner yields the corresponding free acid. Melting point 115°–117° C.

In the same manner are prepared:
1,3-bis-[4-(2-carboxy-ethenyl)phenyl]propane diethyl ester;
1,3-bis[4-(2-carboxy-ethyl)phenyl]propane diethyl ester;
1,3-bis-[4-(2-carboxy-ethyl)phenyl]propane.

We claim:
1. A compound of the formula:

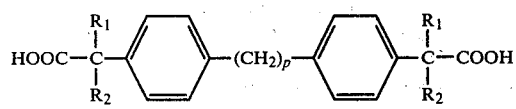

or a pharmaceutically acceptable salt or ester selected from the group consisting of alkyl esters of from 1-4 carbon atoms, phenylethyl esters, phenylpropyl esters, cinnamyl esters and benzyl esters thereof, wherein:
 (a) $R_1$ is alkyl of 1–4 carbon atoms;
 (b) $R_2$ is selected from the group consisting of hydrogen or alkyl of from 1–4 carbon atoms; and
 (c) p has the value of 3 or 4.

2. A compound of the formula:

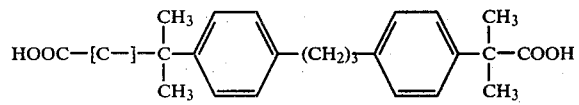

or a pharmaceutically acceptable salt or ester selected from the group consisting of alkyl esters of from 1–4 carbon atoms, phenylethyl esters, phenylpropyl esters, cinnamyl esters and benzyl esters thereof.

3. A pharmaceutical composition having hypocholesterolaemic and hypotriglycerolaemic properties comprising a hypotriglycerolaemically and hypocholesterolaemically effective amount of a compound of this formula:

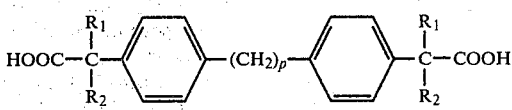

or a pharmaceutically acceptable salt or ester selected from the group consisting of alkyl esters of from 1–4 carbon atoms, phenylethyl esters, phenylpropyl esters, cinnamyl esters and benzyl esters thereof, wherein:
 (a) $R_1$ is alkyl of 1–4 carbon atoms;
 (b) $R_2$ is selected from the group consisting of hydrogen or alkyl of from 1–4 atoms;
 (c) p has the value of 3 or 4; and
 a non-toxic pharmaceutically acceptable carrier.

4. A pharmaceutical composition having hypocholesterolaemic and hypotriglycerolaemic properties comprising a hypocholesterolaemically and hypotriglycerolaemically effective amount of a compound of the formula:

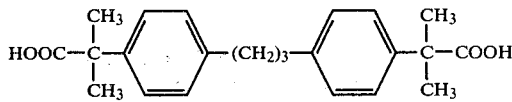

or a pharmaceutically acceptable salt or ester selected from the group consisting of alkyl esters of from 1–4 carbon atoms, phenylethyl esters, phenylpropyl esters, cinnamyl esters and benzyl esters thereof; and
a non-toxic pharmaceutically acceptable carrier.

* * * * *